US009682198B2

(12) United States Patent
Vedrine et al.

(10) Patent No.: US 9,682,198 B2
(45) Date of Patent: Jun. 20, 2017

(54) INTRADERMAL INJECTION DEVICE

(71) Applicant: Becton, Dickinson and Company, Franklin Lakes, NJ (US)

(72) Inventors: Lionel Vedrine, Palo Alto, CA (US); Paul G. Alchas, Franklin Lakes, NJ (US); Peter W. Heyman, Florham Park, NJ (US); Laurent Barrelle, Saint Nizier du Moucherotte (FR); Marina S. Korisch, Wayne, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 59 days.

(21) Appl. No.: 14/568,526

(22) Filed: Dec. 12, 2014

(65) Prior Publication Data

US 2015/0100022 A1  Apr. 9, 2015

Related U.S. Application Data

(63) Continuation of application No. 10/569,618, filed as application No. PCT/US2004/002783 on Jan. 30, 2004, now abandoned.

(Continued)

(51) Int. Cl.
*A61M 5/46* (2006.01)
*A61M 5/28* (2006.01)
(Continued)

(52) U.S. Cl.
CPC ............... *A61M 5/46* (2013.01); *A61M 5/343* (2013.01); *A61M 5/28* (2013.01); *A61M 5/31511* (2013.01);
(Continued)

(58) Field of Classification Search
CPC .... A61M 5/46; A61M 5/3129; A61M 5/3134; A61M 5/34; A61M 5/343; A61M 5/349
See application file for complete search history.

(56) References Cited

U.S. PATENT DOCUMENTS 1,934,046 A   11/1933 Demarchi
2,588,623 A   3/1952 Eliscu et al.
(Continued)

FOREIGN PATENT DOCUMENTS

DE          46325      2/1889
DE         958766      2/1957
(Continued)

*Primary Examiner* — Andrew Gilbert
(74) *Attorney, Agent, or Firm* — The Webb Law Firm

(57) ABSTRACT

An intradermal injection device comprising a unitary body having an open distal end and a proximal end having a skin engaging surface defined thereon, a reservoir defined between the proximal and distal ends for accommodating a drug substance, and a channel defined at the proximal end of the unitary body and extending through, and distally from, the skin engaging surface to the reservoir. A needle cannula having a sharpened proximal end and a distal end may be provided in the channel. The needle cannula is secured in the channel with the distal end being in communication with the reservoir and the proximal end of the needle cannula extending from the skin engaging surface a distance in the range of about 0.5 mm to 3.0 mm such that the skin engaging surface limits penetration of the proximal end of the needle cannula to the dermis layer of the skin of a patient.

20 Claims, 5 Drawing Sheets

Related U.S. Application Data

(60) Provisional application No. 60/498,508, filed on Aug. 28, 2003.

(51) Int. Cl.
    *A61M 5/315*   (2006.01)
    *A61M 5/32*    (2006.01)
    *A61M 5/34*    (2006.01)
    *A61M 5/42*    (2006.01)
    *A61M 5/31*    (2006.01)

(52) U.S. Cl.
    CPC ............ *A61M 5/321* (2013.01); *A61M 5/349* (2013.01); *A61M 5/425* (2013.01); *A61M 2005/311* (2013.01)

(56) References Cited

U.S. PATENT DOCUMENTS

| | | |
|---|---|---|
| 2,876,770 A | 3/1959 | White |
| 3,073,306 A | 1/1963 | Linder |
| 3,390,678 A * | 7/1968 | Lewis ................ A61M 5/28 604/240 |
| 3,400,715 A | 9/1968 | Pederson |
| 3,688,764 A | 9/1972 | Reed |
| 3,797,490 A | 3/1974 | Hurschman et al. |
| 4,014,797 A * | 3/1977 | Raines ................ A61M 5/162 210/446 |
| 4,040,421 A * | 8/1977 | Young ................ A61M 5/343 604/192 |
| 4,270,537 A | 6/1981 | Romaine |
| 4,304,241 A | 12/1981 | Brennan |
| 4,373,526 A | 2/1983 | Kling |
| 4,468,223 A | 8/1984 | Minagawa et al. |
| 4,512,767 A | 4/1985 | Denance |
| 4,769,003 A | 9/1988 | Stamler |
| 4,774,948 A | 10/1988 | Markham |
| 4,795,445 A * | 1/1989 | Jensen ................ A61M 5/34 604/240 |
| 4,834,704 A | 5/1989 | Reinicke |
| 4,883,573 A | 11/1989 | Voss et al. |
| 4,886,499 A | 12/1989 | Cirelli et al. |
| 4,898,588 A | 2/1990 | Roberts |
| 4,955,871 A | 9/1990 | Thomas |
| 4,978,344 A | 12/1990 | Dombrowski et al. |
| 5,137,516 A | 8/1992 | Rand et al. |
| 5,141,496 A | 8/1992 | Dalto et al. |
| 5,147,328 A | 9/1992 | Dragosits et al. |
| 5,190,521 A | 3/1993 | Hubbard et al. |
| 5,195,526 A | 3/1993 | Michelson |
| 5,222,949 A | 6/1993 | Kaldany |
| 5,267,963 A | 12/1993 | Bachynsky |
| 5,328,483 A | 7/1994 | Jacoby |
| 5,417,662 A | 5/1995 | Hjertman et al. |
| 5,505,694 A | 4/1996 | Hubbard et al. |
| 5,527,288 A | 6/1996 | Gross et al. |
| 5,578,014 A | 11/1996 | Erez et al. |
| 5,672,883 A | 9/1997 | Reich |
| 5,679,355 A | 10/1997 | Alexander et al. |
| 5,766,124 A | 6/1998 | Polson |
| 5,848,991 A | 12/1998 | Gross et al. |
| 5,858,001 A | 1/1999 | Tsals et al. |
| 5,873,856 A | 2/1999 | Hjertman et al. |
| 5,883,668 A | 3/1999 | Kazama et al. |
| 5,902,278 A | 5/1999 | Aguilar |
| 5,997,501 A | 12/1999 | Gross et al. |
| 6,004,299 A | 12/1999 | Arai et al. |
| 6,033,387 A | 3/2000 | Brunel |
| 6,099,504 A | 8/2000 | Gross et al. |
| 6,146,361 A | 11/2000 | DiBiasi et al. |
| 6,200,291 B1 | 3/2001 | Di Pietro |
| 6,203,529 B1 | 3/2001 | Gabriel et al. |
| 6,210,361 B1 | 4/2001 | Kamen et al. |
| 6,319,224 B1 | 11/2001 | Stout et al. |
| 6,428,528 B2 | 8/2002 | Sadowski et al. |
| 6,494,865 B1 | 12/2002 | Alchas |
| 6,565,553 B2 | 5/2003 | Sadowski et al. |
| 6,569,143 B2 | 5/2003 | Alchas et al. |
| 6,595,960 B2 * | 7/2003 | West ................ A61M 5/34 604/181 |
| 6,689,100 B2 | 2/2004 | Connelly et al. |
| 6,808,506 B2 * | 10/2004 | Lastovich ......... A61M 5/14244 604/47 |
| 6,843,781 B2 | 1/2005 | Alchas et al. |
| 6,971,999 B2 * | 12/2005 | Py ................ A61M 5/425 604/115 |
| 7,077,830 B2 | 7/2006 | Higaki et al. |
| 7,556,615 B2 * | 7/2009 | Pettis ................ A61M 5/28 604/117 |
| 7,981,081 B2 * | 7/2011 | Marsh ................ A61M 5/204 604/117 |
| 8,021,511 B2 * | 9/2011 | Erskine ................ A61M 5/34 156/294 |
| 8,267,890 B2 * | 9/2012 | Alchas ................ A61M 5/3129 604/115 |
| 8,496,862 B2 | 7/2013 | Zelkovich et al. |
| 8,721,603 B2 | 5/2014 | Lundquist |
| 2001/0011171 A1 | 8/2001 | Alchas |
| 2001/0012925 A1 | 8/2001 | Alchas |
| 2002/0007811 A1 | 1/2002 | Kinoshita et al. |
| 2002/0045866 A1 | 4/2002 | Sadowski et al. |
| 2002/0052580 A1 | 5/2002 | Ooyauchi |
| 2002/0068909 A1 * | 6/2002 | Alchas ................ A61M 5/46 604/198 |
| 2002/0072709 A1 | 6/2002 | Sadowski et al. |
| 2002/0156426 A1 * | 10/2002 | Gagnieux ............ A61M 5/326 604/197 |
| 2002/0193740 A1 | 12/2002 | Alchas et al. |
| 2002/0193778 A1 | 12/2002 | Alchas et al. |
| 2003/0014018 A1 | 1/2003 | Giambattista et al. |
| 2003/0050602 A1 * | 3/2003 | Pettis ................ A61M 5/28 604/117 |
| 2003/0093032 A1 | 5/2003 | Py et al. |
| 2003/0100885 A1 | 5/2003 | Pettis et al. |
| 2003/0187395 A1 | 10/2003 | Gabel et al. |
| 2003/0199822 A1 | 10/2003 | Alchas et al. |
| 2003/0212379 A1 | 11/2003 | Bylund et al. |
| 2005/0033234 A1 * | 2/2005 | Sadowski ............ A61M 5/2033 604/140 |
| 2005/0113753 A1 | 5/2005 | Alchas et al. |
| 2005/0256499 A1 | 11/2005 | Pettis et al. |
| 2007/0005017 A1 * | 1/2007 | Alchas ................ A61M 5/14244 604/117 |
| 2008/0045900 A1 | 2/2008 | Alchas et al. |
| 2010/0270702 A1 | 10/2010 | Zelkovich et al. |
| 2012/0010573 A1 | 1/2012 | Lundquist |
| 2013/0138047 A1 | 5/2013 | Takemoto et al. |

FOREIGN PATENT DOCUMENTS

| | | |
|---|---|---|
| DE | 29918794 U1 | 2/2000 |
| FR | 2612401 A1 | 9/1988 |
| GB | 2321014 A | 7/1998 |
| JP | 113862 B2 | 3/1989 |
| JP | 200037456 A | 2/2000 |
| WO | 9302726 | 2/1993 |
| WO | 9309826 | 5/1993 |
| WO | 9413342 | 6/1994 |
| WO | 9423777 | 10/1994 |
| WO | 9501198 | 1/1995 |
| WO | 9927986 | 6/1999 |
| WO | 0128613 A1 | 4/2001 |
| WO | 0147586 A1 | 7/2001 |
| WO | 0193931 A1 | 12/2001 |
| WO | 02083215 A1 | 10/2002 |
| WO | 03022330 A2 | 3/2003 |
| WO | 03066126 A2 | 8/2003 |

* cited by examiner

INTRADERMAL INJECTION DEVICE

This application is a continuation of U.S. patent application Ser. No. 10/569,618, now abandoned, which was a National Stage Entry of PCT/US04/02783 filed Sep. 30, 2004 which claims priority from Provisional Application No. 60/498,508, filed Aug. 28, 2003.

FIELD OF THE INVENTION

The present invention relates to an intradermal injection device.

BACKGROUND

Drug substances may be delivered into a patient's body via injection into the muscle, subcutaneous tissue, or into the epidermis and dermis (also referred to as an intradermal injection). The efficacy of a particular drug substance may change when the drug is delivered intradermally. In some cases, intradermal delivery may be more beneficial to the patient. There is considerable variation in the skin thickness both between individuals and within the same individual at different sites of the body. Generally, the outer skin layer epidermis has a thickness of ranging from 50 to 200 microns, and the dermis, the inner and thicker layer of the skin, has a thickness ranging from 1.5 to 3.5 mm. Therefore, a needle cannula that penetrates the skin deeper than about 3 mm has a potential of passing through the dermis layer of the skin, thus making the injection into the subcutaneous region, which may result in an insufficient immune response, especially where the substance to be delivered intradermally has not been indicated for subcutaneous injection. Also, the needle cannula may penetrate the skin at too shallow a depth to deliver the substance and result in what is commonly known in the art as a "wet injection" due to reflux of the substance from the injection site.

The standard procedure for making an intradermal injection, generally referred to as the Mantoux procedure, is difficult to perform, and successful administration of an intradermal injection using that procedure depends upon experience and technique of the person using the injection device. The Mantoux procedure requires that the user of the injection device stretch the skin, orient the needle bevel to face upwardly, and insert a 26 gauge short bevel needle cannula to deliver a volume of 0.5 ml or less of the drug substance into the skin of the patient. During this procedure, the needle cannula must be maintained at an angle varying from around 10° to 15° with respect to the patient's skin to form a blister or wheal in which the drug substance is deposited or otherwise contained. The above-described technique is difficult to perform and typically requires the attention of a trained nurse or medical doctor. Inserting the needle to a depth greater than about 3 mm typically results in a failed intradermal injection because the drug substance being expelled through the cannula will be injected into the subcutaneous tissue of the patient.

As disclosed in United States Patent Application Publication No. 2002/0068909 A1, which published on Jun. 6, 2002, and U.S. Pat. No. 6,494,865 B1, which issued on Dec. 17, 2002, both to the assignee herein, an intradermal needle assembly has been developed for use with a prefillable container having a reservoir capable of storing a drug substance for injection into the skin of a patient. A needle cannula is supported by the prefillable container and has a forward tip extending away from the container. The intradermal needle assembly includes a limiter that is securable to the prefillable container and which surrounds the needle cannula and provides a generally flat skin engaging surface extending in a plane generally perpendicular to an axis of the needle cannula. The flat skin engaging surface is adapted to be received against the skin of the patient during administration of the intradermal injection. The needle forward tip extends beyond the skin engaging surface a distance of approximately 0.5 to 3 mm. Therefore, the limiter limits penetration of the needle into the dermis layer of the skin of the patient so that the drug substance is injected into the dermis layer of the patient.

SUMMARY OF THE INVENTION

The present invention is directed to an intradermal injection device comprising a unitary body having an open distal end and a proximal end having a skin engaging surface defined thereon; a reservoir defined between the proximal and distal ends for accommodating a drug substance; and a channel defined at the proximal end of the unitary body and extending through, and distally from, the skin engaging surface to the reservoir. Further, the device comprises a needle cannula having a sharpened proximal end and a distal end. The needle cannula is secured in the channel with the distal end being in communication with the reservoir and the proximal end of the needle cannula extending from the skin engaging surface a distance in the range of about 0.5 mm to 3.0 mm such that the skin engaging surface limits penetration of the proximal end of the needle cannula to the dermis layer of the skin of a patient.

In a further aspect of the subject invention, a protrusion is provided on the proximal end of the body of the device which extends proximally from a first surface portion. Preferably, the protrusion is annular and circumscribes the channel. The protrusion aides in the injection process by providing a good interface between the device and the patient's skin, limiting leakage from the injection site during the injection process.

In yet a further aspect of the subject invention, a holder for a medicament comprising the unitary body is provided to which a needle cannula may be affixed.

Advantageously, with the subject invention, a needle cannula is "staked" or directly affixed to an injection body or holder for a medicament to form an intradermal injection device, without the use of a separate limiter. The subject invention is particularly well-suited to be used as a glass prefillable intradermal syringe, although other applications are possible.

As used herein, distal shall refer to a part or direction located away or furthest from a patient, whole proximal shall refer to a part or direction towards or located nearest to a patient. Also, a drug substance is used herein in an illustrative, non-limiting manner to refer to any substance injectable into the body of a patient for any purpose. Reference to a patient may be to any being, human or animal.

These and other features of the subject invention shall be better understood through a study of the following detailed description and accompanying drawings.

BRIEF DESCRIPTION OF THE DRAWINGS

In the drawings, which are not to scale, and in which like reference characters denote similar elements throughout the several views.

DETAILED DESCRIPTION OF THE PREFERRED EMBODIMENTS

Figure 1:
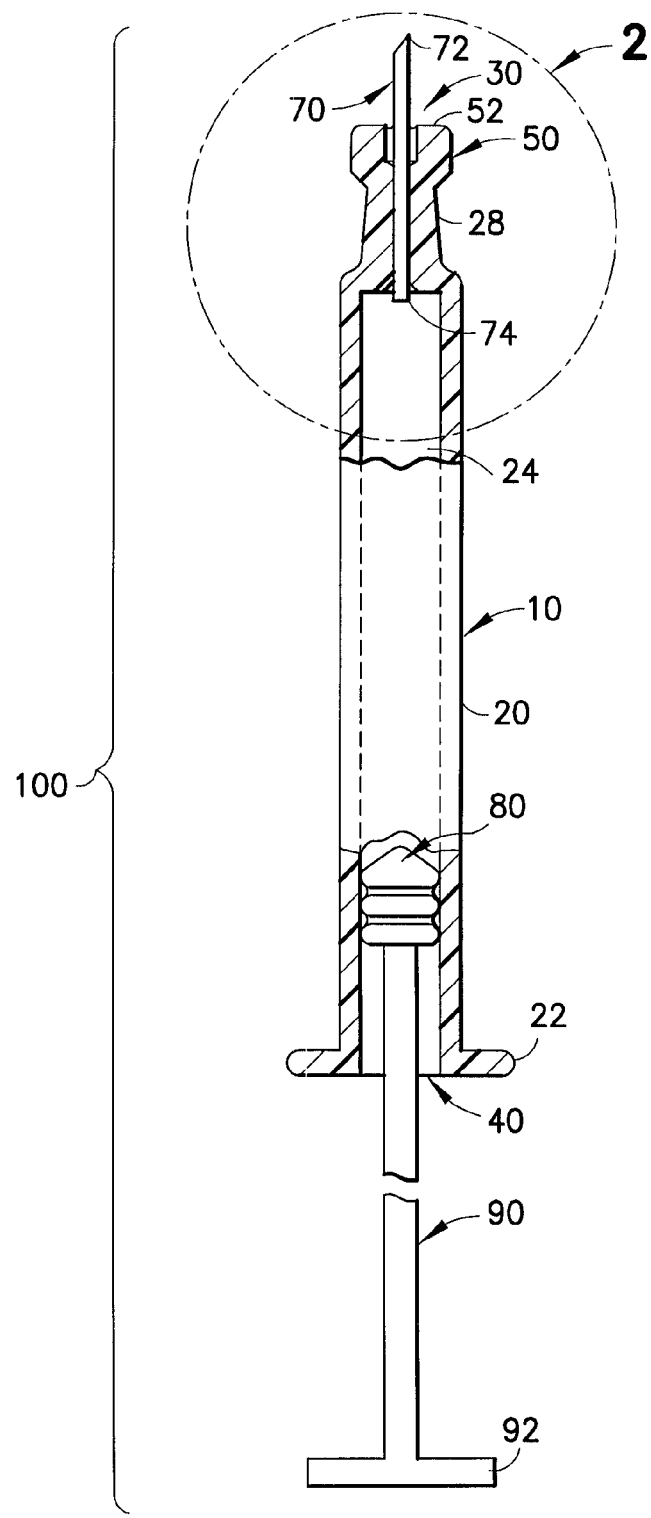
FIG. 1 is a side partial cross-sectional view of an intradermal injection device constructed in accordance with an embodiment of the present invention.
Figure 2:
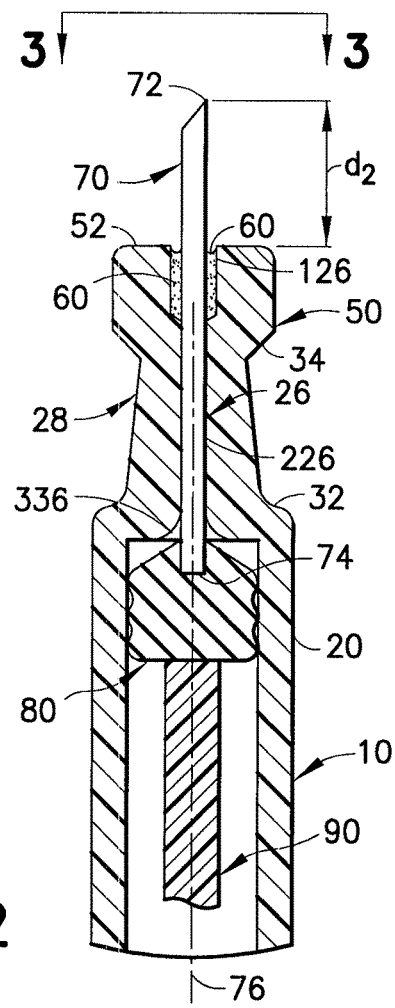
FIG. 2 is an enlarged partial view of Section 2 in FIG. 1.
Figure 3:
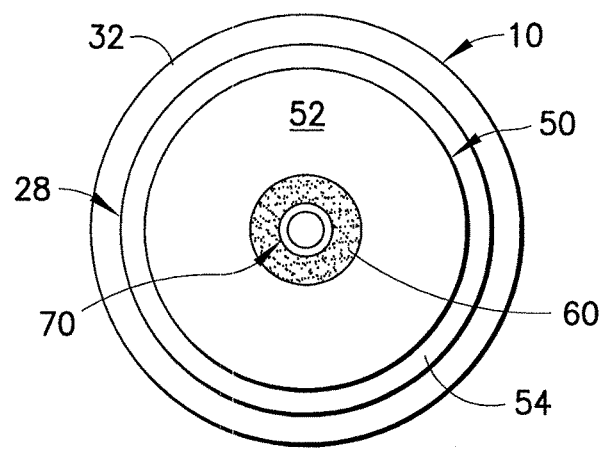
FIG. 3 is a top view of the intradermal injection device depicted in FIG. 2, as viewed from line 3-3.

FIGS. 1-3 depict an intradermal injection device 100 constructed in accordance with an embodiment of the present invention. The injection device 100 is preferably a syringe comprised of a body 10 having a barrel 20, an open distal end 40 with a flange 22, a proximal end 30, and a reservoir 24 defined therebetween. A drug substance may be placed in the reservoir 24 before the injection device 100 is provided to the end user. The injection device 100 also includes a plunger 80 slidingly and sealingly provided within the reservoir 24, and a plunger rod 90 secured to the plunger 80 to facilitate movement of the plunger 80 within the reservoir 24 to effect expulsion of the drug substance therefrom.

The body 10 narrows near the proximal end 30 to form a neck 28 that supports a limiter 50 defined at the proximal end 30 of the body 10. The neck 28 is preferably tapered, particularly to converge in a distal to proximal direction. A first transition 32 may be provided to accommodate a gradual change in the outer diameter between the barrel 20 and the neck 28, and a second transition 34 may be provided to accommodate a gradual change in outer diameter between the neck 28 and limiter 50. The transitions 32, 34 may be chamfered, radiused, or otherwise softened to avoid forming sharp, e.g., right angle, transitions between the various elements.

The limiter 50 defines a skin engaging surface 52 at its proximal end that contacts the skin of a patient during use of the injection device 100. The limiter 50 and skin engaging surface 52 are unitarily formed with the body 10. The skin engaging surface 52 may be formed flat or with any known configuration, including, but not limited to, those surface configurations disclosed in U.S. application Ser. No. 10/543,714, the entire disclosure of which is incorporated herein by reference.

Figures 4, 5:
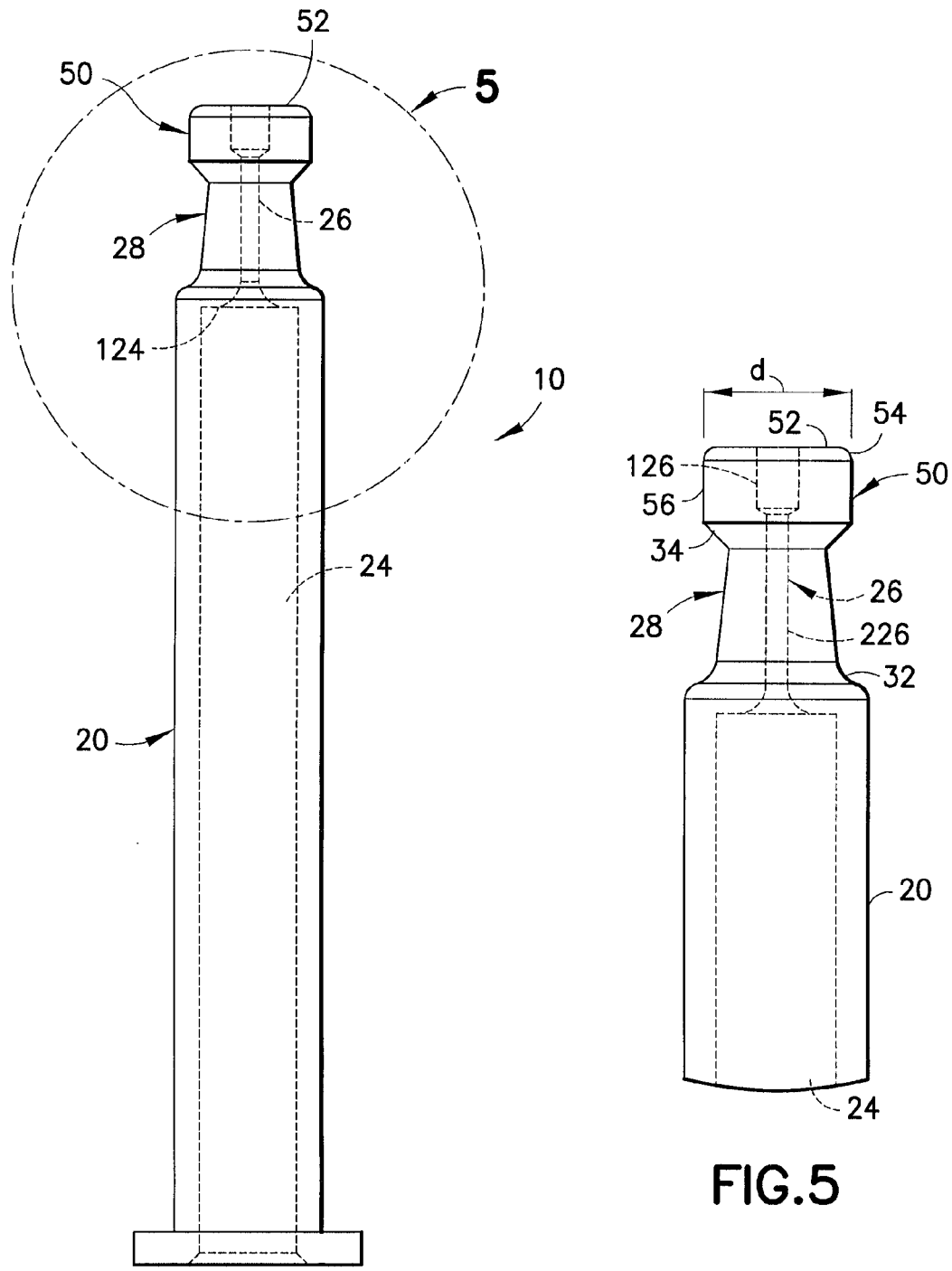
FIG. 4 is an elevational side view of a body of an intradermal injection device, constructed in accordance with an embodiment of the present invention.
FIG. 5 is an enlarged partial view of Section 5 in FIG. 4.
Figure 6:
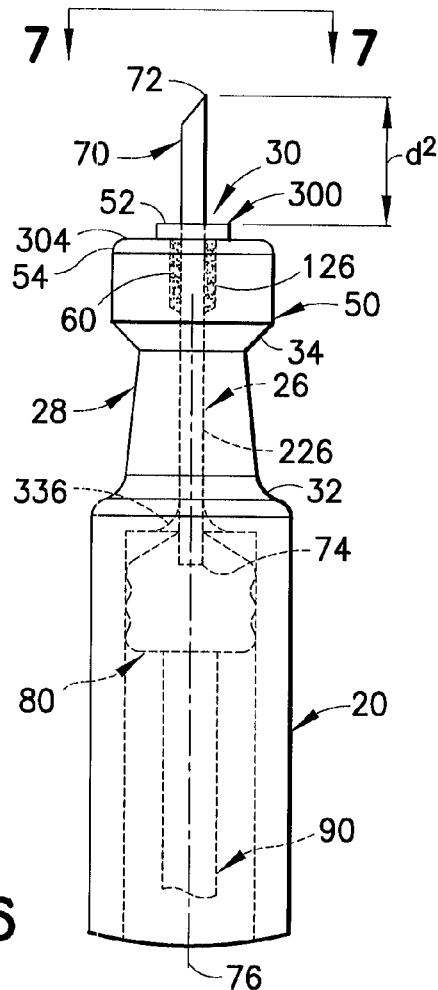
FIG. 6 is a partial side view of a body of an intradermal injection device having a protrusion extending therefrom constructed in accordance with an embodiment of the present invention.
Figure 7:
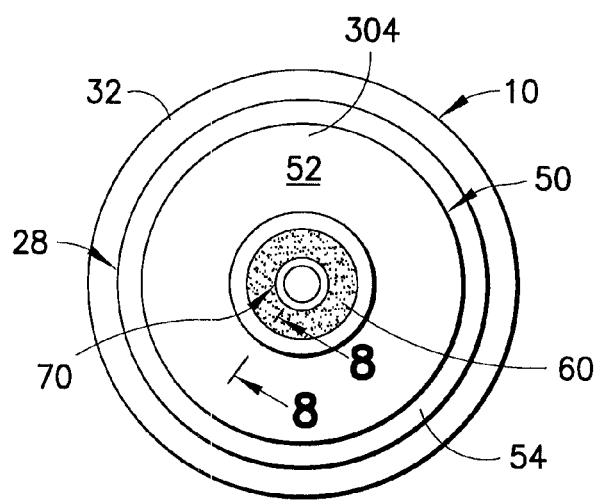
FIG. 7 is a top view of the intradermal injection device depicted in FIG. 6, as viewed from line 7-7.
Figure 8:
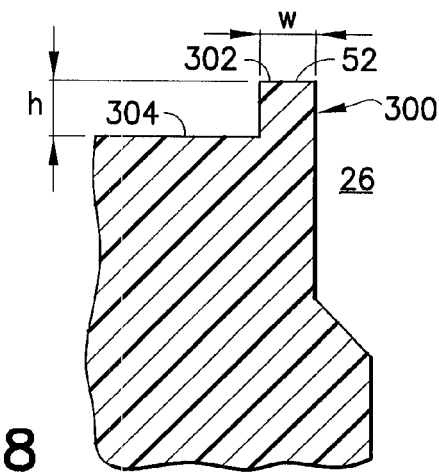
FIG. 8 is a cross-sectional view taken from line 8-8 of FIG. 7 without the needle cannula or adhesive being shown; and, FIGS. 9a-9b depict various cross-sections which may be used alternatively to the cross-section shown in FIG. 8.

With reference to FIG. 5, the limiter 50 preferably has a cylindrical shape and defines an outer diameter d which is less than or equal to 11 mm, more preferably less than or equal to 5.5 mm. Outer perimeter 54, formed at the intersection of the skin engaging surface 52 and side surface 56 of the limiter 50, is preferably chamfered, radiused or otherwise softened to avoid defining a sharp transition between the skin engaging surface 52 and the side surface 56.

A channel 26 extends through the skin engaging surface 52 and in a distal direction into communication with the reservoir 24. The channel 26 preferably has a central longitudinal axis which is generally perpendicular to a plane defined by the skin engaging surface 52. The channel 26 may have a constant diameter, or it may have a diameter varying in size from one approximately matched to the outer diameter of a needle cannula, and increasing to a size greater than the outer diameter of the needle cannula. In either case, a portion of the channel 26 preferably has a diameter sized and shaped to accommodate a needle cannula, as described in more detail below. For a varying diameter channel 26, it is preferred that the end of the channel 26 nearest the skin engaging surface 52 have a larger diameter than other portions of the channel 26 to receive an adhesive for securing the needle cannula in the channel 26. Also, for a varying diameter configuration, the cross-sectional profile of the channel 26 may be tapered, stepped, or any other configuration that permits variation in the diameter of the channel 26. In a preferred embodiment, such as is depicted in FIG. 2, channel 26 has a first part 126 located near the skin engaging surface 52, and a second part 226, located near the reservoir 24. The first part 126 has a diameter greater than that of the second part 226; the diameter of the second part 226 being preferably selected to be approximately the same as the outer diameter of the needle cannula provided as part of the inventive injection device 100. The outer diameter of the various gauges of needle cannula is well known in the art and the second part 226 may be sized accordingly. The channel 26 may optionally include a third part 336 provided adjacent the reservoir 24 to provide an at least partial transition between a bottom surface 124 of the reservoir 24 and the second part 226 of the channel 26. A similar transition may be provided between the first and second parts 126, 226 of the channel 26.

As shown in FIGS. 4 and 5, the body 10, which can act as a holder for medicament, can be provided alone. The body 10 in combination with a needle cannula 70 forms the injection device 100.

With reference to FIGS. 1 and 2, the needle cannula 70 is supported at the proximal end 30 of the body 10 in the channel 26 and includes a distal end 74 located in or near the reservoir 24 and a forward tip 72, preferably sharpened, that extends a predetermined distance $d_2$ from the skin engaging surface 52. In a preferred embodiment, distance $d_2$ ranges from approximately 0.5 mm to 3 mm. The distance $d_2$ is preferably measured from a plane defined by coplanar portions of the skin engaging surface 52 (whether or not the skin engaging surface 52 is flat), more preferably, the distance $d_2$ is measured from proximalmost portions of the skin engaging surface 52. The coplanar portions may be disposed continuously or discontinuously about the needle cannula 70. Preferably, the skin engaging surface 52 is formed to engage a patient's skin such that a uniform ring of pressure is generated about the needle cannula 70 during injection. The ring of pressure assists in reduction in fluid leakage from the injection site during the injection process.

The distal end 74 is in fluid communication with the reservoir 24, and the needle cannula 70 provides a fluid path from the reservoir 24 through which the drug substance may be expelled from the injection device 100 and injected into the intradermal region in a patient's skin. A central axis of the needle cannula 70, indicated as reference character 76 in FIG. 2, is arranged at a predetermined angle with respect to a plane defined by the skin engaging surface 52, particularly the plane from which the distance $d_2$ is measured as described above. In a preferred embodiment, that predetermined angle is approximately 90°. Other angular relationships are also contemplated by, and within the scope and spirit of, the present invention. Moreover, the angular relationship between the needle cannula central axis 76 and plane of the skin engaging surface 52 may be defined by variation on the placement of the needle cannula 70 in the channel 26, variation in the orientation of the skin engaging surface 52, or variation of both.

The needle cannula 70 is secured to the body 10 and within the channel 26 using a suitable adhesive 60 (see, e.g., FIG. 3), particularly where the body 10 is formed of glass. In a preferred embodiment, the adhesive 60 is heat or ultraviolet curable. The amount of adhesive 60 used to secure the needle cannula 70 within the channel 26 is controlled so as to ensure that the flatness of the skin engaging surface 52 is not affected by the adhesive 60. Preferably, the amount of adhesive 60 provided does not completely fill the first part 126 of the channel 26, but instead, is recessed with regard to the skin engaging surface 52, e.g. by forming a generally concave surface. The first part 126 of the channel 26 conveniently provides a pocket for the adhesive 60 and it is not necessary to apply the adhesive 60 to other portions of the channel 26. As will be appreciated by those skilled in the art, the needle cannula 70 can be directly secured in the channel 26 using any known technique, such as being insert molded with the body 10 being formed of plastic.

The plunger rod 90 is connected at one end to the plunger 80 and having, at its other end, a thumb pad 92 that may be depressed by a user to cause movement of the plunger 80 within the reservoir 24 to expel the drug substance therefrom. When the plunger 80 is caused to move within the reservoir 24, the drug substance housed in the reservoir 24 is caused to be expelled therefrom. The plunger 80 may come into contact with the bottom surface 124 of the reservoir 24. Optionally, the plunger 80 may be forced onto the distal end 74 of the needle cannula 70 to sealingly engage the needle cannula 70. With this arrangement, the plunger 80 may thus seal the needle cannula 70 and prevent additional drug substance or other material from exiting the needle cannula 70 (either into the patient's skin or elsewhere).

It is preferred that the body 10 of the inventive intradermal delivery device 100 be at least partially made from glass, preferably wholly, although other suitable materials that may be now known or hereafter developed may be used, including plastic. Although the inventive intradermal delivery device 100 may be used in various applications, it is particularly well-suited as a glass prefillable intradermal syringe.

In use, a drug substance is provided into the reservoir 24 and the plunger 80 is placed in the open distal end 40 of the barrel 20. As will be recognized by those skilled in the art, with the device being a prefilled device, the device 100 will be provided to a point-of-use with the drug substance and the plunger 80 being in the barrel 20 ready for use. With the device 100 not being prefilled, the plunger 80 is prepared and the drug substance is charged into the barrel by aspiration or other known methods at the point of use. Once ready, the inventive injection device 100 is preferably oriented in a generally perpendicular relationship with respect to the injection site. Thus, the central axis 76 of the needle cannula 70 is generally perpendicular to a plane defined by the patient's skin at the injection site. Deviations from generally perpendicular typically will not adversely impact the use and efficiency of the inventive injection device 100. The forward tip 72 of the needle cannula 70 is caused to pierce the patient's skin until the skin engaging surface 52 contacts the patient's skin. The length of the needle cannula 70 extending beyond the skin engaging surface 52 and the skin engaging surface 52 itself serve to limit the depth of penetration of the forward tip 72 of the needle cannula to the intradermal space of the patient's skin. Upon full insertion, the health care provider administering the injection depresses the thumb pad 92 to cause the plunger 80 to move in a distal to proximal direction in the reservoir 24 thus causing expulsion of the drug substance therefrom. Typically, the entire contents of the reservoir 24 are administered in a single dose. That is, each injection device 100 may be filled with a predetermined dose of a particular drug substance intended for administration in a single dose. Once the drug substance has been effectively expelled and administration of the injection is complete, the plunger 80 may be forced to sealingly engage the distal end 74 of the needle cannula 70 and prevent further expulsion of drug substance or other material through and from the needle cannula 70.

Although not shown in the figures, the inventive injection device 100 may also include a safety component that shields the forward tip 72 of the needle cannula 70 to reduce the possibility of accidental needle-stick injury from occurring after use of the device 100. The safety component may cover the forward tip 72 before use and/or after use, and preferably locks in place after use to prevent inadvertent exposure to the forward tip 72 after use of the device 100. The safety component may comprise a holder for the body 10, a shield to cover the forward tip 72 of the needle cannula 70, other components that facilitate manual or assisted activation, or variations and combinations thereof.

With reference to FIGS. 6-9*b*, and in a further aspect of the subject invention, a protrusion 300 is provided to extend proximally from the proximal end of the body 10. As indicated above, the skin engaging surface 52 may be formed with various configurations. Here, the skin engaging surface 52 is defined on a free proximal end 302 of the protrusion. A first surface portion 304 is also defined on the proximal end 30 of the body 10. Preferably, the first surface portion 304 is flat, annular, and circumscribes the protrusion 300. The protrusion 300 is preferably annular and circumscribes the channel 26. More preferably, the protrusion 300 bounds to channel 26, particularly the first part 126. With the skin engaging surface 52 being defined on the protrusion 300, the surrounding first surface portion 302 provides a wider base for stability during an injection.

The protrusion 300 may be formed with various cross-sectional shapes. In a most preferred embodiment, and with reference to FIG. 8, the protrusion is formed with a rectangular cross-section, particularly a square cross-section. The height h may be in the range of 0.2 mm to 0.5 mm and the width w of the free proximal end 302, and thus the skin engaging surface 52, may be in the range of 0.2 mm to 0.5 mm. Of course, with a square cross-section, the height h and width w are generally equal.

Figure 9A:
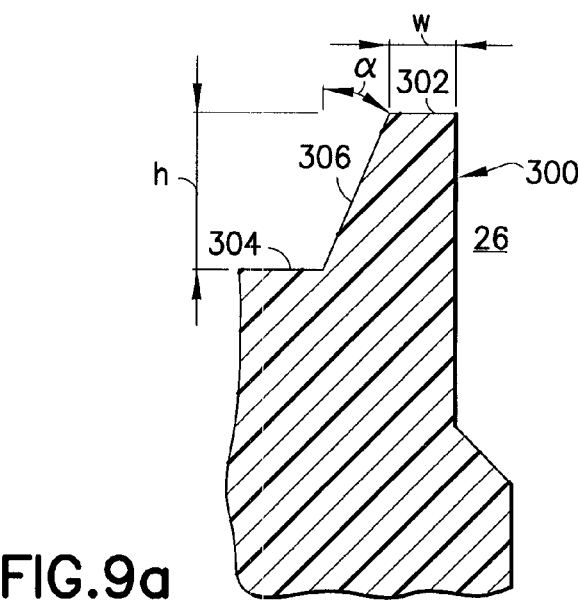
Figure 9B:
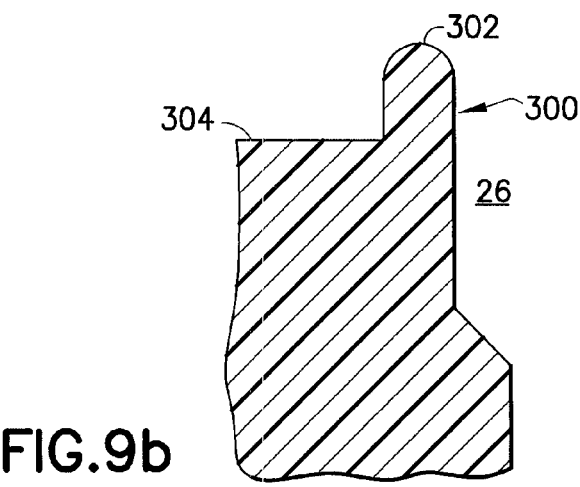

Other cross-sectional shapes are possible for the protrusion 300. With reference to FIG. 9*a*, the protrusion 300 may have a trapezoidal cross-section with a height h in the range of 0.5 mm to 1.0 mm, a width w of the free proximal end 302 in the range of 0.35 mm to 0.6 mm, and a side surface 306 disposed at an angle α relative to the first surface portion 304, the angle α being in the range of 30-45 degrees. Other polygonal shapes are possible. Also, portions of the protrusion 302 may be formed arcuately as shown in FIG. 9*b*.

As indicated above, it is preferred to bound the channel 26 with the protrusion 300. With the body 10 being formed of glass, and as will be appreciated by those skilled in the art, the transition between the skin engaging surface 52 and the channel 26 shown in the embodiment of FIGS. 1-5 is difficult to achieve. In particular, a pin or other element used to form the channel 26 easily disrupts the transition and consistency in formation may be difficult to achieve. With forming the body 10 of glass, it has been found that the protrusion 300 allows for easier and more consistent formation of the channel 26 and surrounding portions. The protrusion 300 (ring) is added to compensate for the radius which normally forms between the tip and the channel during the glass forming process. The result is a sharper corner.

While the invention has been described in relation to the preferred embodiments with several examples, it will be understood by those skilled in the art that various changes may be made without deviating from the spirit and scope of the invention as defined in the appended claims.

What is claimed is:

1. An intradermal injection device comprising:
   a unitary body, wherein said unitary body is formed wholly from glass, said unitary body having an open distal end and a proximal end having a skin engaging surface defined thereon and a protrusion extending therefrom, wherein at least a portion of the cross-section of the protrusion is arcuate, a reservoir defined between said distal and proximal ends for accommodating a drug substance, and a channel defined at said proximal end of said unitary body and extending through, and distally from, said skin engaging surface to said reservoir; and
   a needle cannula having a sharpened proximal end and a distal end, said needle cannula being secured in said channel with said distal end being in communication with said reservoir and said proximal end of said needle cannula extending from said protrusion a distance in the range of about 0.5 mm to 3.0 mm,
   wherein said protrusion continuously circumscribes said needle cannula and bounds said channel such that said skin engaging surface and said protrusion limits penetration of said proximal end of said needle cannula to the dermis layer of the skin of a patient.

2. The device as in claim 1, wherein said channel has a cross-sectional shape having a non-constant width.

3. The device as in claim 2, wherein said channel has a first portion located proximate to said skin engaging surface and a second portion located proximate to said reservoir, said first portion having a larger cross-sectional width than said second portion.

4. The device as in claim 3, wherein said needle cannula is secured in said channel with an adhesive, said adhesive being disposed in said first portion.

5. The device as in claim 1, wherein said unitary body comprises a barrel having the open distal end, said reservoir being defined in said barrel, a neck portion adjacent a proximal end of said barrel, and a limiter adjacent a proximal end of said neck portion, said first surface portion being defined on a proximal end of said limiter.

6. The device as in claim 5, wherein said barrel has a first outer diameter, said neck portion has a second outer diameter, and said limiter has a third outer diameter.

7. The device as in claim 6, wherein said outer diameter of said neck portion is tapered.

8. The device as in claim 5, wherein said limiter has an outer diameter that is no greater than 11 mm.

9. The device as in claim 5, wherein said limiter has an outer diameter that is no greater than 5.5 mm.

10. The device as in claim 1, wherein said skin engaging surface defines a plane disposed perpendicularly to a longitudinal axis of said needle cannula.

11. The device as in claim 1, wherein said skin engaging surface comprises portions that are coplanar and that are disposed about said needle cannula.

12. The device as in claim 11, wherein said coplanar portions are disposed continuously about said needle cannula.

13. The device as in claim 11, wherein said coplanar portions are disposed discontinuously about said needle cannula.

14. The device as in claim 11, wherein said coplanar portions are defined on proximalmost portions of said skin engaging surface.

15. The device as in claim 1, further comprising a plunger slidably disposed in said reservoir.

16. The device as in claim 15, wherein said plunger sealingly engages said distal end of said needle cannula upon a predetermined extent of sliding movement in said reservoir.

17. The device as in claim 15, further comprising a plunger rod for selective attachment to said plunger, said plunger rod being configured to force sliding movement of said plunger within said reservoir.

18. The device as in claim 1, wherein said needle cannula is secured in said channel with an adhesive.

19. The device as in claim 18, wherein said adhesive is recessed in said channel below said skin engaging surface.

20. The device as in claim 1, wherein an inner edge of said continuous protrusion is provided adjacent an entire circumference of said channel.

* * * * *